Jan. 15, 1946. P. D. SLOCUM Plant Pat. 666
WATER LILY PLANT
Filed Dec. 26, 1944
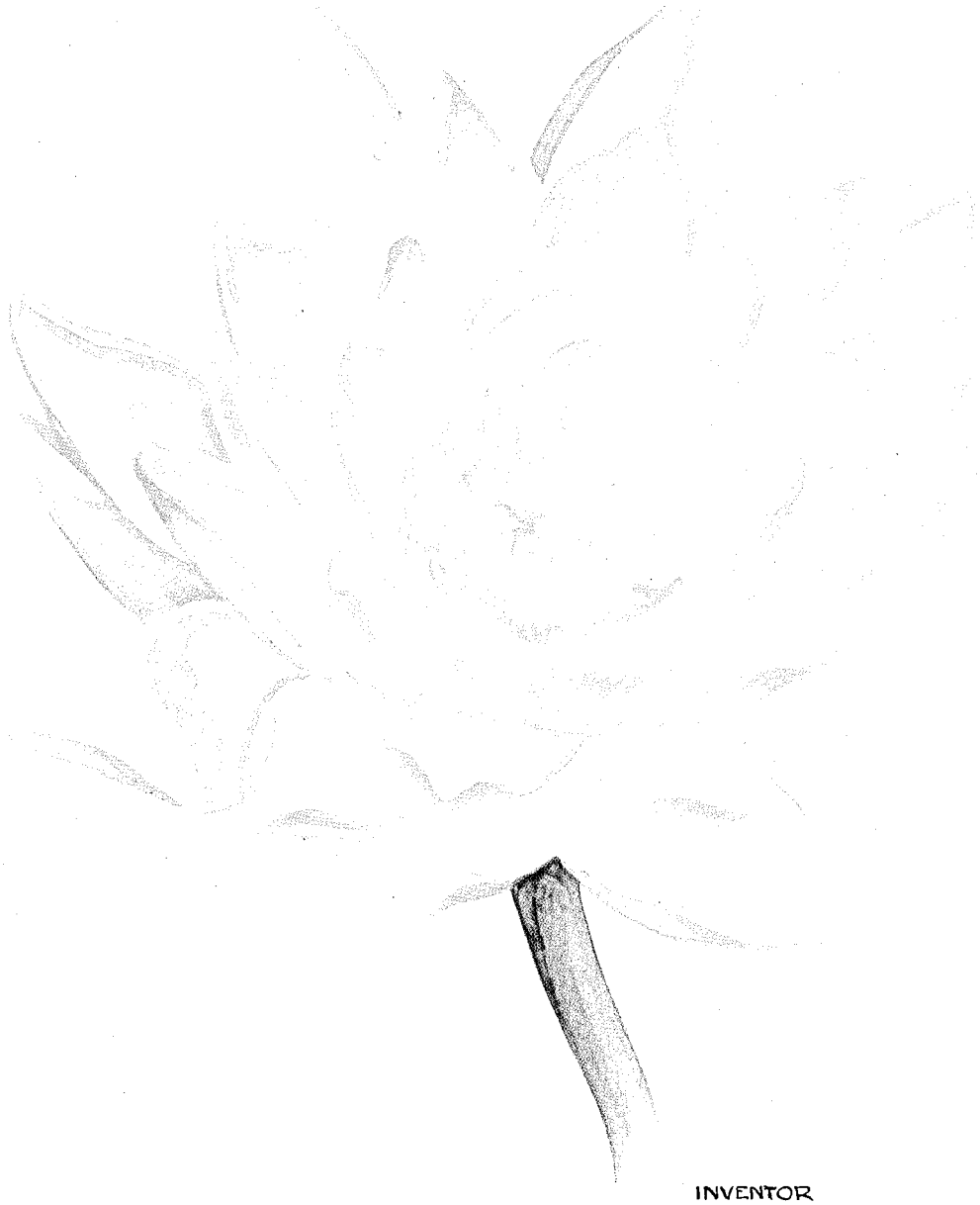
INVENTOR
Perry D. Slocum
By Orville M. Kile
PLANT PATENT AGENT Patented Jan. 15, 1946

Plant Pat. 666

UNITED STATES PATENT OFFICE

666

WATER-LILY PLANT

Perry D. Slocum, Cortland County, N. Y.

Application December 26, 1944, Serial No. 569,823

1 Claim. (Cl. 47—60)

My present invention relates to a new and distinct variety of hardy hybrid day-blooming water lily plant in the light pink class.

The principal object of my invention is improvement in petal shape and retention of flower color, both of which are well demonstrated in the new variety. The really outstanding feature of my new variety is the non-fading quality of its light pink flowers. Whereas most light pink varieties fade to a dirty white on the second day, this new variety retains its pink coloring for fully five days. The center of the flower is a rich golden yellow.

My new variety resulted from a cross between the varieties Pink Opal and Marliac Rose. Since one parent is of the Odorata type and the other of the Tuberosa type, a new type as well as variety has been produced which blooms more freely and is more double than the average Odorata but does not have as marked fragrance as is usually present in that type of lily. The new variety has been asexually reproduced through several generations and its characteristics have proved to be permanent.

The illustrations which accompany this specification, show a specimen of my new variety in approximately its true colors and slightly enlarged in the original painting.

Following is a detailed description of my new water lily variety. Color plate references indicate Ridgway's Color Standards and Nomenclature.

*The plant*

Leaves:

*Color.*—The young leaves, up to about two weeks after reaching the surface of the water, are approximately Hay's Russet (Pl. XIV) on the under side except for the central portion and the prominent veins which are approximately Serpentine Green (Pl. XVI). Upper side of young leaves is very glossy and almost entirely Victoria Lake (Pl. L). The older leaves are glossy and approximately Cedar Green (Pl. VI) on the upper side, with an under side that is bronzed in the center and approximately Liver Brown (Pl. XIV) toward the edges.

*Shape.*—Almost truly orbicular except for the wedge-shaped opening to the center. Lobes are very acute and not overlapping. Margins smooth and flat.

*Size.*—Full grown leaf averages 10 to 12 inches in diameter.

Stems: Serpentine Green (Pl. XVI) to Grass Green.

*The flower*

Petalage: Averages 38 to 40 petals. This number is greater than the average of similar water lilies which usually have about 28 to 30 petals.

Size: Large, 5 to 6 inches in diameter.

Color: General tonal effect is light pink. Petals are between Rose Pink and Deep Rose Pink (Pl. XII) at the base, graduating to almost white at the tips. The color remains approximately the same for five days after the flower opens. This feature is in contrast with other known light pink water lilies which fade to a dirty white on the second day.

Fragrance: Slight and very pleasing.

Petal shape: The petals are long and slender and very pointed. Edges of most petals roll upward much as those of the Rose Arey.

Sepals: Four; not very prominent.

Stamens: About a hundred deep yellow stamens are bunched in the center of each flower.

Flower form: Around the bunched stamens are very small rudimentary petals which in turn are surrounded by larger petals graduated in size toward the outer rim of the corolla.

*The bud*

Color: Bronzed green.

Shape: Pointed.

Size: Typical buds are about 2½ inches long.

*Comparison*

The varieties most nearly like my new variety are Morning Glory and Mrs. C. W. Thomas, but these differ from the present variety principally in the following respects:

1. Flowers of my new variety have more slender and more pointed petals.

2. The edges of most of the petals of flowers of my new variety roll upwards much as do those of Rose Arey, while the petals of these two varieties are not noticeably rolled.

3. The color of the flowers of my new variety is deeper and richer than that of either Morning Glory or Mrs. C. W. Thomas.

4. The pink color of the flowers of my new variety is retained for five days after opening, whereas the flowers of these other two varieties as well as of most other known light pink varieties fade almost white on the second day.

Having thus disclosed my invention, I claim:

The new and distinct variety of hybrid, hardy day-blooming water lily plant herein shown and described, characterized particularly by its flowers which have narrow slender petals rolled upward at the edges and a delicate light pink color which lasts for at least five days.

PERRY D. SLOCUM.